United States Patent [19]
Gordon

[11] Patent Number: 5,733,122
[45] Date of Patent: Mar. 31, 1998

[54] DENTAL IMPLANT ATTACHMENT ASSEMBLY INCLUDING DEVICE AND METHOD FOR RESISTING LOOSENING OF ATTACHMENT

[76] Inventor: Basil Gordon, 4 Gunnison, Irvine, Calif. 92715

[21] Appl. No.: 454,601

[22] Filed: May 31, 1995

[51] Int. Cl.⁶ .................................................. A61C 8/00
[52] U.S. Cl. ................................................ 433/172; 433/173
[58] Field of Search ..................................... 433/172, 173, 433/174, 175, 176

[56] References Cited

U.S. PATENT DOCUMENTS

| | | | |
|---|---|---|---|
| 4,631,031 | 12/1986 | Richter | 433/173 |
| 4,713,003 | 12/1987 | Symington et al. | 433/173 |
| 4,840,529 | 6/1989 | Phillips | 411/397 |
| 4,850,873 | 7/1989 | Lazzara et al. | 433/220 |
| 4,854,873 | 8/1989 | Linden | 433/173 |
| 5,076,788 | 12/1991 | Niznick | 433/174 |
| 5,106,300 | 4/1992 | Voitik | 433/173 |
| 5,108,288 | 4/1992 | Perry | 433/173 |
| 5,116,225 | 5/1992 | Riera | 433/174 |
| 5,145,371 | 9/1992 | Jörnéus | 433/173 |
| 5,169,308 | 12/1992 | Kvist | 433/172 |
| 5,180,303 | 1/1993 | Hornberg et al. | 433/174 |
| 5,199,873 | 4/1993 | Schulte et al. | 433/174 |
| 5,209,666 | 5/1993 | Balfour et al. | 433/173 |
| 5,282,746 | 2/1994 | Sellers et al. | 433/172 |
| 5,286,195 | 2/1994 | Clostermann | 433/173 |
| 5,302,125 | 4/1994 | Kownacki et al. | 433/172 |
| 5,342,199 | 8/1994 | Gillespie | 433/173 |
| 5,350,302 | 9/1994 | Marlin | 433/174 |
| 5,368,480 | 11/1994 | Balfour et al. | 433/174 |
| 5,417,569 | 5/1995 | Perisse | 433/174 |
| 5,439,381 | 8/1995 | Cohen | 433/173 |

FOREIGN PATENT DOCUMENTS

| | | |
|---|---|---|
| 473262 | 3/1992 | European Pat. Off. . |
| 61493 | 1/1994 | Japan . |

OTHER PUBLICATIONS

Zest Anchors Pproduct Catalog.

Primary Examiner—Cary E. O'Connor
Attorney, Agent, or Firm—Brown, Martin, Haller & McClain

[57] ABSTRACT

An attachment assembly for securing a dental prosthetic device to an implant includes a post having a through bore which is adapted to be secured in a recess in the prosthetic device, a primary fastening screw having a head for engagement in the through bore and a threaded shaft for projecting out of the through bore for threaded engagement in a correspondingly threaded bore of an implant or implant abutment, and a locking insert member for securing in the post through bore above the primary screw with a lower end face of the insert member bearing against the upper end face of the screw head in order to resist loosening of the screw member once fastened to the implant.

30 Claims, 3 Drawing Sheets

DENTAL IMPLANT ATTACHMENT ASSEMBLY INCLUDING DEVICE AND METHOD FOR RESISTING LOOSENING OF ATTACHMENT

BACKGROUND OF THE INVENTION

The present invention relates generally to dental implant attachment assemblies, and is particularly concerned with an implant attachment assembly including a locking device for resisting loosening of a primary fastening screw securing a prosthetic device to a dental implant.

Dental implants are surgically implanted in a patient's jawbone to provide anchors for prosthetic devices such as crowns, bridges, dentures and the like. Typically, the prosthetic device is secured to the implant by means of a primary screw traversing the prosthetic device which engages the female threading of the implant. A post is conventionally molded into the prosthetic device during manufacture, the post having a through bore for receiving the primary screw. The threaded shaft of the primary screw projects out of the post and prosthetic superstructure for threaded engagement in the implant bore. One problem with such arrangements is that the primary fastening screw tends to loosen, rendering the attached prosthesis unstable and loose.

SUMMARY OF THE INVENTION

It is an object of the present invention to provide a new and improved implant attachment assembly and method for resisting loosening of the primary fastening screw of a dental implant arrangement.

According to one aspect of the present invention, an attachment assembly for attaching to a dental implant is provided which comprises a post member having an upper end, a lower end, and a through bore with a step in diameter defining a seating shoulder, a fastening screw having a head for seating in the through bore against the seating shoulder and a threaded shaft for projecting out of the through bore through the lower end of the post member for engagement in a matching threaded bore in an implant or implant abutment. A locking insert member is provided for securing in the through bore above the head of the fastening screw, the head of the fastening screw having an upper face and the lower end of the insert member having a lower face for engagement with the upper face of the fastening screw when the insert member is secured in the through bore, and a locking mechanism for releasably securing the insert member in the through bore with the lower face of the insert member abutting the upper face of the screw head.

Any suitable releasable locking mechanism may be provided between the insert member and through bore. For example, the insert member and through bore may be provided with interengageable screw threads along some or all of their length. Alternatively, a bayonet locking mechanism may be provided. In another embodiment, the insert member is expandable into frictional locking engagement with the walls of the through bore. This has the advantage that no modification to the existing bore or channel in a post is needed, and the device can be retro-fitted to existing implant secured prosthetic devices. In another alternative, the through bore may be provided with a groove and ball bearings mounted in radial channels in the insert member may be biassed partially into the groove to lock the insert member in the desired position in which it bears against the upper face of the fastening screw.

The insert member may be of softer material than the fastening screw, for example a softer metal or a more resilient plastic material, so that it can be compressed up against the upper face of the fastening screw head and further resist rotation or loosening of the screw. The upper face of the screw head and mating lower face of the insert member may each have surface roughening, or alternatively may be ridged or grooved to increase friction between the abutting surfaces and thus further resist loosening of the screw.

The mating fastener formations may be mating screw threads of different pitch from the threads on the fastener screw, or may be any other type of locking formation such as bayonet lugs and grooves. The upper face of the screw head typically has a recess shaped to receive the end of an appropriate tool for tightening or loosening the screw, for example a hex-shaped recess for receiving the end of a hex tool. Preferably, the insert member has a through bore for access to the screw head by the tool when the insert member is placed in the through bore. The through bore may also be shaped for mating with the end of an appropriate tool for locking the insert member in the through bore or releasing it when desired. Alternatively, the insert member may have spaced peripheral cut outs at its upper end for receiving an appropriate tightening tool.

Instead of providing a separate insert member, the head of the primary screw may be elongated and provided with a locking surface mateable with opposing portions of the post through bore.

According to another aspect of the present invention, a method of securing a primary fastening screw in an implant to resist loosening of the screw is provided, which comprises the steps of: inserting the fastening screw into a bore in a post member with the threaded shaft of the screw projecting out of the lower end of the post member, engaging the threaded shaft in a correspondingly threaded bore of an implant, tightening the screw until the head of the screw engages a seating shoulder in the post member and the screw is secured to the implant, inserting a locking device into the bore in the post member above the fastening screw, and engaging fastener formations on the insert device with mating fastener formations in the bore to secure the insert device in the bore and simultaneously move the lower face of the locking device into abutment with the upper face of the screw head, whereby the abutment between the opposing faces of the locking device and screw head acts to resist any screw-loosening rotation of the fastening screw.

As noted above, the insert or locking device preferably has a through bore to permit access to a tool-receiving recess in the upper face of the screw head while the insert is secured or positioned in the bore, so that the screw can be tightened or loosened without first removing the insert. The primary screw may be tightened first, and the insert or locking device may then be tightened down into close abutment with the upper face of the primary screw.

The implant attachment assembly of this invention allows the primary fastening screw which secures a prosthetic device to an implant to be made more secure against accidental loosening with use. The insert or locking device is secured in close engagement with the upper face of the screw so as to resist any movement of the screw, and thus resists loosening of the screw.

BRIEF DESCRIPTION OF THE DRAWINGS

The present invention will be better understood from the following detailed description of some preferred embodiments of the invention, taken in conjunction with the accompanying drawings, in which like reference numerals refer to like parts, and in which.

DESCRIPTION OF THE PREFERRED EMBODIMENTS

FIGS. 1–4 of the drawings illustrate an implant attachment assembly according to a first embodiment of the present invention. The assembly is used to attach a dental prosthetic device such as a crown, bridge or other superstructure 10 to an implant 12 embedded and osseointegrated into jaw bone 14. The assembly basically comprises a post or cylinder 16 having a through bore 18, a primary fastening screw 20 seated in the lower end of the bore 18 for securing the post 16 to implant 12, and a locking insert or element 22 for securing in the bore above the screw 20 to resist loosening of the screw.

Figures 1, 2, 3, 4, 5, 6, 7, 8:
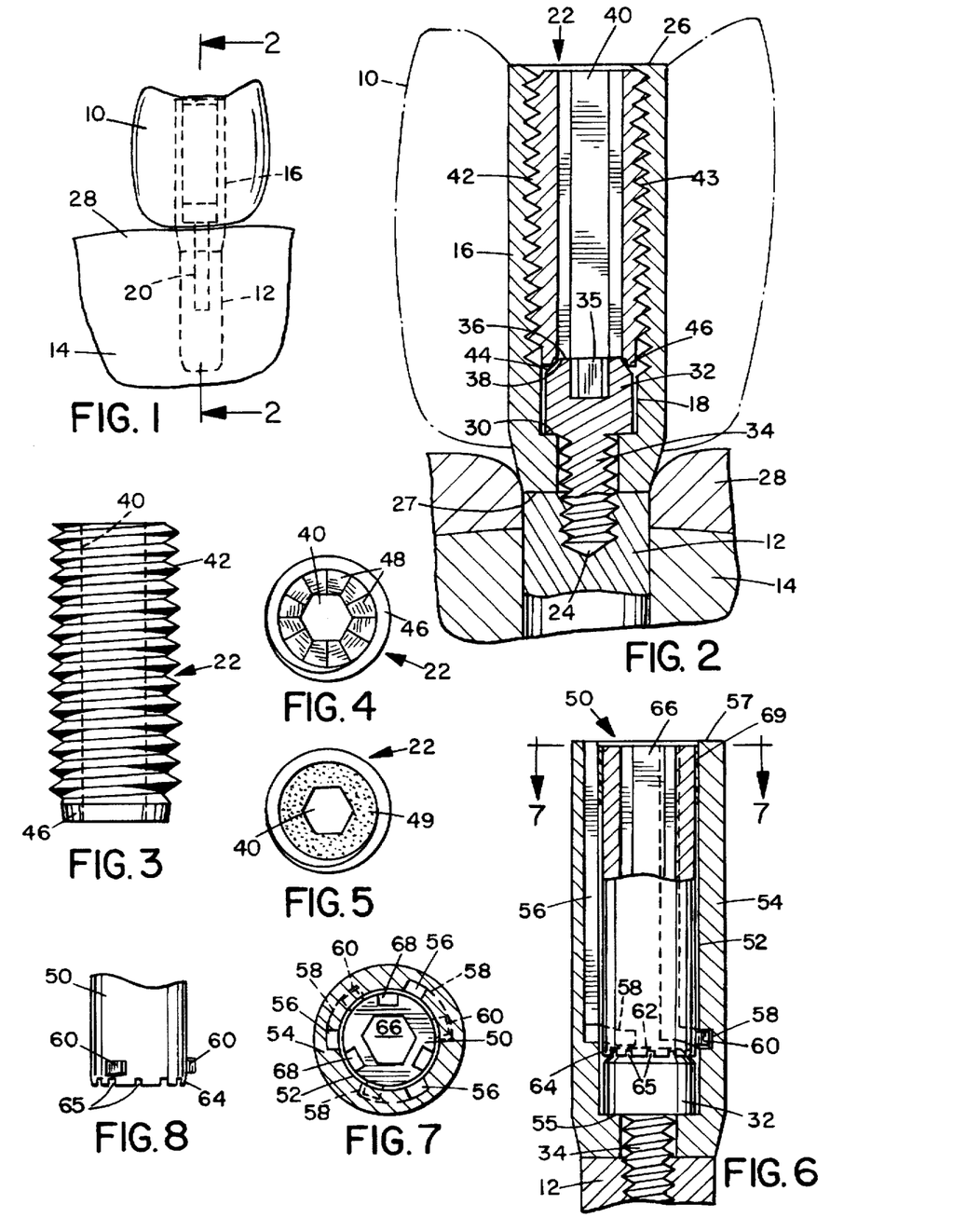
FIG. 1 illustrates a typical dental implant with an attachment assembly according to one embodiment of the present invention securing a prosthetic superstructure to the implant.
FIG. 2 is an enlarged sectional view taken on line 2—2 of FIG. 1.
FIG. 3 is a side view of the locking insert, showing an optional frictional tip.
FIG. 4 is a bottom end view of the locking element, showing gripping grooves.
FIG. 5 is a bottom end view showing surface roughening for frictional grip.
FIG. 6 is a sectional view similar to FIG. 2, showing an alternative twist lock bayonet-type attachment of the locking insert.
FIG. 7 is a sectional view taken on line 7—7 of FIG. 6.
FIG. 8 is a side view of the lower end of the locking insert.

Various types of dental implants are known which are designed to be implanted in a prepared bore in the jawbone and which have a bore 24 for attaching a superstructure to the implant directly or implant abutment indirectly. Typically, the implant bore 24 is threaded for connection to a fastening screw, although different types of implants have screw threads of differing pitch, direction, and depth. The post or cylinder 16 has an upper end 26 and a lower end 27 for abutment with the upper end of implant 12, or abutment where the tissue or gum 28 has a thickness above the implant which is relatively small. Conventionally, where the gum is relatively thick, a gingival collar or the like will be secured between the implant and post 16, in which case the lower end of the post will engage the upper end of the collar in a similar manner. The post is designed to be embedded and secured in the dental prosthetic device or superstructure 10 by an adhesive or the like, with the upper end of the post exposed.

Through bore 18 extends between the upper and lower end of the post with a step in diameter 30 adjacent the lower end which separates a larger diameter, upper portion of the bore from the smaller diameter, lower end of the bore. The primary fastening screw has a head 32 of diameter slightly less than that of the larger diameter portion of bore 18, and a smaller diameter, threaded shaft 34 with threads of dimensions matching those of the implant bore 24, or a threaded bore in a gingival collar, if used. The smaller diameter, lower end portion of bore 18 is of larger diameter than the threads of shaft 34 so that the shaft may project freely through the lower end portion of the bore. The step 30 forms a seat for the head 32 of the shaft with the shaft projecting through the lower end portion and out of the lower end of the post for threaded engagement in implant bore 24, as best illustrated in FIG. 2. Head 32 has a conventional recess 35 in upper face 36 for receiving the end of a suitable tool for use in tightening the screw into the implant bore. The recess may be hexagonal, for example, for receiving a hex driver tool.

Locking insert 22 is designed to fit into the upper end of the bore 18 above the screw so that it bears against the upper face of the screw to resist loosening once the screw is secured in the implant bore. Suitable interengageable mating formations are provided in the bore 18 and on the outer surface of insert 22 for securing the insert in the bore. Insert 22 comprises a generally cylindrical member of diameter matching that of the upper portion of bore 18 and having a lower face 38 for bearing against the upper face 36 of the screw head. The insert 22 has a through bore 40 of diameter equal to or larger than that of the recess 35 at the upper end of the screw head. Bore 40 may also be of hexagonal shape, as best illustrated in FIG. 4, for engagement with an appropriate tool for securing the insert in the bore 18.

The insert 22 has screw threads 42 on its outer cylindrical surface which match the threads 43 on the inner surface of bore 18. The threads 42, 43 are of different dimensions to those on the shaft 34, for example of different pitch, depth and/or orientation. Although the threads extend along the entire length of the insert 22 as illustrated in FIGS. 2 and 3, they may alternatively extend along only part of the length of the insert from lower end 38. The threads must extend over a sufficient distance to provide a sufficient locking force, and preferably extend for a length of at least 1.5 mm. The remainder of the insert member may have a smooth, cylindrical surface. Similarly, the threads 43 on the inner surface of bore 18 may extend over only part of the length of the larger diameter portion of the bore, and not up to the upper end 26 as in the illustrated embodiment. If the insert 22 only has threads at the lower end for a length of about 1.5 mm, the bore 18 will be threaded upwardly to the upper end of the cylinder from a location just below the upper end 36 of screw head 32.

The screw head 32 preferably has a bevelled upper edge 44, as illustrated in FIG. 2. The insert member may have a reduced diameter, annular skirt 46 at its lower end which is designed to engage over the bevelled edge 44 as illustrated in FIG. 2 with the lower end 38 in abutment with the upper end face of the screw head. Preferably, some type of surface roughening or other formations are provided on the upper end face 36 of the screw head and the mating lower end face 38 of the locking insert, to ensure good frictional contact between these faces. For example, as illustrated in FIG. 4, the end faces may have alternating radial ribs 48 and grooves. Alternatively, as illustrated in FIG. 5, the end faces may have surface roughening 49 provided by sand blasting or the like. Any alternative types of surface roughening, such as ridges, grooves, knurling or the like, may be provided in order to produce good frictional contact between the faces and to resist relative rotation between the parts when engaged.

The post 16, screw 20 and locking insert 22 may be of any suitable material. The post and screw are preferably of a suitable metal for dental use, and the insert 22 may be of the same material. However, the insert 22 is preferably of softer metal or other softer material than that of screw 20, so that it can be deformed into closer mating engagement with the screw head.

In order to assemble the implant attachment as illustrated in FIG. 2, the fastening screw is first inserted through bore 18 so that the projecting end of shaft 34 engages in implant bore 24, using a suitable hex tool to tighten the screw into the implant. When the screw is several turns away from full engagement in bore 24, the locking insert is threaded into the bore 18, using a similar hex tool of larger dimensions, until it is several turns away from full engagement. The first screw is then tightened down as far as it will go, and the insert 22 in turn is tightened down until the lower end 38 is pressed into close frictional engagement with the upper face 36 of screw 20.

In an alternative arrangement, the through bore 40 may have a lower end portion of smaller dimensions matching those of recess 35, whereby the same hex tool may be used to tighten both parts. The screw 20 is first tightened until it is a few turns away from full engagement. The hex tool is then engaged with the lower, smaller end portion of bore 40 and the insert is tightened until it is two or three turns away from engagement. The tool is then inserted through the insert 22 and into the recess 35, and rotated to fully tighten the screw into the implant bore. The tool is then retracted back into engagement with the appropriate portion of bore 40, and rotated to tighten down the locking insert on top of the screw.

With this arrangement, the locking insert bears down against the upper end of the screw and resists any screw-loosening rotation due to the close frictional engagement between the lower end face of the insert and the upper end face of the screw. Because the threads of the locking insert are of different pitch and have other differing parameters from those on the screw, the two parts cannot loosen simultaneously.

The length and diameter of the locking insert will vary depending on the type of implant system and superstructure with which it is to be used. Different length locking inserts may be provided for different superstructure applications, or the insert length may be custom cut or adjusted at the upper end by the operator using standard dental instrumentation. Inserts may also be provided in different diameters depending on the diameter of the bore or channel in the post with which they are to be used. Similarly, the diameter of the through bore 40 in insert 22 will vary depending on the insert diameter as well as the diameter of the tool-receiving recess at the upper end of the screw. Generally, the insert will be provided in a range of lengths from 1.5 mm to 15 mm.

Nylon or similar coatings may be applied to the fitting surfaces of the primary fastening screw 20, the locking insert 22, and the threaded surfaces of the post and implant, to reduce vibratory shock to the system and also to reduce the ingress of saliva into the system. A locking washer may also be provided under the head of the primary screw for providing additional locking force to resist loosening.

FIGS. 6–8 illustrate an alternative embodiment in which a locking insert 50 is secured in a bore 52 of a post 54 by means of a bayonet connection rather than screw threads. The locking insert 50 bears against a primary fastening screw 20 which is identical to that of the previous embodiment, and like reference numerals have been used for like parts as appropriate. Screw 20 secures the post 54 to an implant 12 or a gingival collar in the conventional manner, as discussed above.

In this embodiment, as in the first embodiment, the post 54 has a step 55 in diameter separating the larger diameter upper portion of the bore from the lower end portion of the bore, through which the threaded shaft 34 of screw 20 projects. The larger diameter portion of the bore has a series of spaced, parallel grooves or channels 56 extending along its length from the upper end 57 to a location which will be spaced just above the upper surface 36 of the screw head. A downwardly inclined, transverse locking slot 58 extends in a generally circumferential direction from the lower end of each channel 56, with a detente at its lowermost end. In the illustrated embodiment, three bayonet channels 56 are provided, although a greater or lesser number may be provided if desired.

The locking insert 50 has three spaced bayonet lugs 60 projecting from its outer surface adjacent the lower end 62 of the insert, for sliding engagement along the bayonet channels 56 as the insert 50 is inserted into bore. Preferably, the lugs 60 have a slight incline or ramped lower surface. Once the lugs 60 reach the lower ends of the respective channels 56, the locking insert is rotated in a clockwise direction, so that the lugs 60 travel along transverse slots 58 and, at the same time, the insert is urged axially downwardly against the upper surface of the screw, due to the incline of the slots 58 and the ramped lug surfaces. The insert is rotated until each lug reaches the detente at the lower end of each slot 58, releasably locking the insert in the bore.

Optionally, the insert 50 has an annular skirt 64 projecting downwardly from lower end 62 of the insert. Skirt 64 is inclined inwardly, as best illustrated in FIG. 8, and has a plurality of castellations or slots 65 around its periphery. As the insert is forced downwardly against the upper end face of the screw head 32, the skirt 64 engages the bevelled edge 44 of the screw head. This forces the skirt to expand resiliently outwardly so that it is wedged between the edge of the screw and the wall of bore 52, further resisting any loosening of the screw 20.

As in the previous embodiment, the insert 50 has a hex-shaped through bore 66 aligned with the hexagonal recess on the upper face of the screw head. Preferably, the insert also has a series of spaced, wrench-receiving slots 68 on its outer surface adjacent the upper end of the insert, as best illustrated in FIG. 7. This allows a wrench-type tool to engage the slots and turn the insert both to lock the bayonet lugs into the receiving slots 58, and to release the insert when desired. An annular plastic sealing sleeve or ring 69 is mounted around the upper end portion of insert 50, as illustrated in FIG. 6, to provide a saliva seal.

With this arrangement, the primary screw can be tightened into the implant. The insert can conveniently be engaged in the bore simply by sliding it vertically downwardly to the bottom of channels 56, and then turning clockwise so that the lugs are forced down along slots 58. This will simultaneously force the insert axially downwardly so that the lower end face is urged into close frictional engagement with the upper face of the screw head. Simultaneously, the skirt 64 is biassed outwardly by the bevelled rim of the screw head and is jammed between the screw head and cylindrical bore. As in the previous embodiment, the upper face of the screw head and abutting lower face of the insert will have suitable surface formations for increased frictional engagement, such as ribs, bumps, knurls or other surface roughening.

When the locking insert is locked in position, any loosening of the screw will be resisted by the engagement of the lower end face of the insert with the screw head. This significantly reduces the risk of the screw becoming loose over time.

Figure 9:
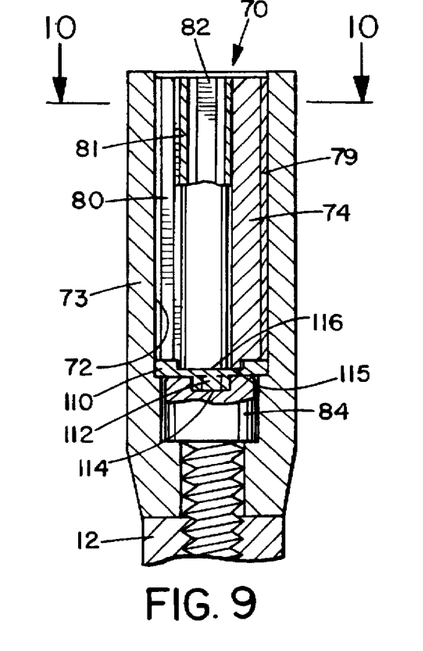
FIG. 9 is a view similar to FIG. 6, showing an alternative expanding insert.
Figure 10:
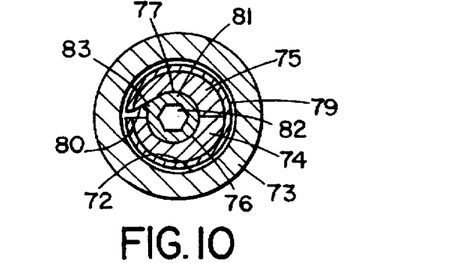
FIG. 10 is a sectional view taken on line 10—10 of FIG. 9, with the insert in unlocked position.
Figure 11:
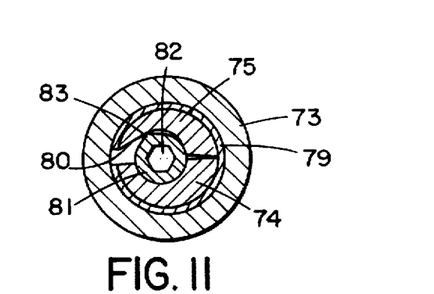
FIG. 11 is a view similar to FIG. 10, with the insert in locked position.

FIGS. 9–11 illustrate another alternative embodiment of the invention in which an insert member 70 can be retrofitted to an existing implant attachment assembly without requiring any modification of the channel or bore 72 in post member 73. The insert member 70 of FIGS. 9–11 comprises two semi-cylindrical halves 74, 75 which have at least partially semi-circular recesses 76, 77 on their mating flat faces which together define a through bore through the insert member. The two halves 74, 75 may optionally be held in a C-shaped metal sleeve or sheath 79. Sleeve 79 may be made with different wall thicknesses so that the insert member can be fitted in different diameter channels 72.

One of the recesses 77 has an eccentric cut-out 80, as best illustrated in FIGS. 10 and 11, and has screw threads for threaded engagement with central actuating screw 81. Screw 81 has a tool-engaging recess 82 at its upper end for engagement with a suitable tightening tool such as a hex driver. Screw 81 has a projecting cam surface 83 which is located in the cut-out 80 when the screw is in an inoperative position, as illustrated in FIG. 10. As in the previous embodiments, the lower end faces of the two halves 74, 75 may have suitable surface roughening or projections for close frictional engagement with the upper end face of fastener screw 84 which secures the assembly to an implant in the same manner as in the previous embodiments. Additionally, because different manufacturers of fastening screws have differently machined hex tool recesses, an intermediate mating joiner 110 is used where the lower side specifically engages the hex recess and its upper side engages the insert, thereby providing a male/female torque-locking mechanism. Joiner 110 has a projecting hex boss 112 for mating engagement in hex bore 114 at the upper end of screw 84, as illustrated in FIG. 9. Cylindrical projection 115 at the lower end of the insert halves 74, 75 engages in a corresponding recess 116 at the upper end of joiner 110. Joiners will be provided with differently machined hex bosses for mating with all conventional fastening screws.

In order to install the insert member, the device is pushed axially downwardly into channel 72 until the lower end face engages the upper end face of screw 84. Screw 81 is then rotated in a clockwise direction, causing cam surface 83 to move out of cut out 80 and urge the insert halves 74, 75 apart, expanding the effective diameter of the insert, as illustrated in FIG. 11. The outer surface of the expanded sleeve 79 will bear against the inner surface of channel 72, and the frictional engagement between the two surfaces will hold the insert member in the channel. Preferably, the sleeve 79 is of copper or other suitable material.

Rather than using a cover to expand the two halves 74, 75, a tapered screw may be used, such that as the screw is screwed into the bore formed by recesses 76, 77, the gradually increasing diameter of the screw will urge the two halves apart.

Figure 12:
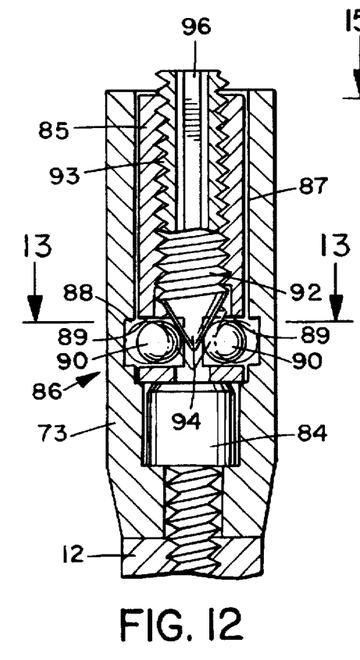
FIG. 12 is a view similar to FIG. 9, with a wedge-type ball lock mechanism.
Figure 13:
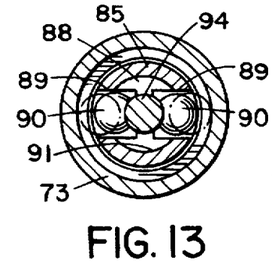
FIG. 13 is a sectional view taken on line 13—13 of FIG. 12.

FIGS. 12 and 13 illustrate another alternative insert member 85 and wedge-type ball locking mechanism 86 for securing the insert member in channel 87 and against the upper end face of primary fastener screw 20. In this embodiment, the channel 87 is provided with an annular groove 88 adjacent the upper end face 36 of screw 20. Insert member 85 has a single or a pair of oppositely directed radial cut-outs or channels 89 adjacent its lower end face and a ball bearing 90 is located in each channel 89. A through bore 91 extends through insert member 85 to intersect the inner ends of cut outs 89. Bore 91 has screw threads at least adjacent its lower end. A secondary screw member 93 having a beveled lower end portion 94 extends through bore 91. Screw member 93 has threads 92 adjacent beveled end portion 94 for threaded engagement with the threads in bore 91. A tool receiving recess 96 is provided in the upper end of screw member 93.

In order to secure the insert member 85 in bore or channel 87, it is slidably inserted into the channel until the lower end face engages the upper end face of the primary screw 84. As in the previous embodiments, the mating end faces may have suitable surface roughening, ribs, grooves or the like for enhanced frictional engagement. At this point the screw 93 is rotated clockwise, moving downwardly such that the beveled portion 94 urges the ball bearings 90 outwardly into groove 88, forcing the insert member downwardly into close mating engagement with the upper end face of the screw 84, and locking the insert member in the channel. Thus, the insert member will resist any loosening of primary screw 84.

Figure 14:
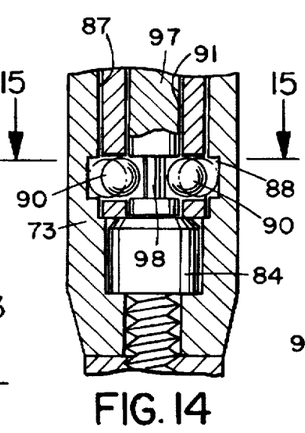
FIG. 14 is a view similar to a portion of FIG. 12, with a cam actuated ball lock mechanism.
Figure 15:
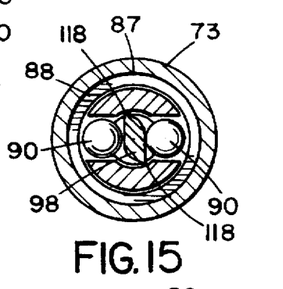
FIG. 15 is a sectional view taken on line 15—15 of FIG. 14, with the ball mechanism unlocked.
Figure 16:
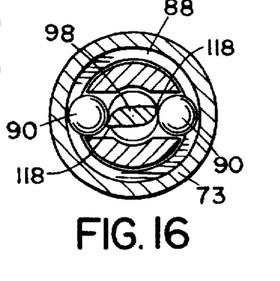
FIG. 16 is a similar sectional view with the ball mechanism unlocked.

FIGS. 14–16 illustrate a modification which is similar to the embodiment of FIGS. 12 and 13 in that a ball lock mechanism is used, in which ball bearings 90 engage in grooves 88 to lock insert member 85 in position, and like reference numerals have been used for like parts as appropriate. However, a cam actuated mechanism is used for urging ball bearings 90 outwardly in this embodiment. Thus, rather than a screw member with a tapered or beveled end portion for urging the ball bearings outwardly, a screw member 97 in threaded bore 91 is secured to a cam member 98 mounted in through bore 91 in alignment with ball bearings 90. In the inoperative position of FIGS. 14 and 15, the ball bearings are in their retracted position. Once the insert member 85 is inserted to a position in which the ball bearings are aligned with groove 88, the screw member 97 is rotated one quarter turn, from the position of FIG. 15 to that of FIG. 16. The cam bears against the ball bearings and forces them outwardly to engage in groove 88, locking the insert member in the channel with the lower end face bearing against the upper end face of the primary screw 84 to resist rotation. A detente mechanism 118 is incorporated in the opposite end faces of the cam to prevent it from unintentionally unlocking.

Although the embodiments of FIGS. 12–16 each use two ball bearings, a single ball bearing may alternatively be used, or a greater number of ball bearings may be used if necessary. In all of the above embodiments, the insert member is releasably locked in the channel of a denture post so as to bear against a primary fastener screw securing the post and denture to an implant or implant abutment, and resist loosening of the primary screw.

Other possible techniques for locking the insert in the bore include a lever mechanism, a gate device or a projection which extends through the side wall of the insert. These devices may be reversibly activated.

Figure 17:
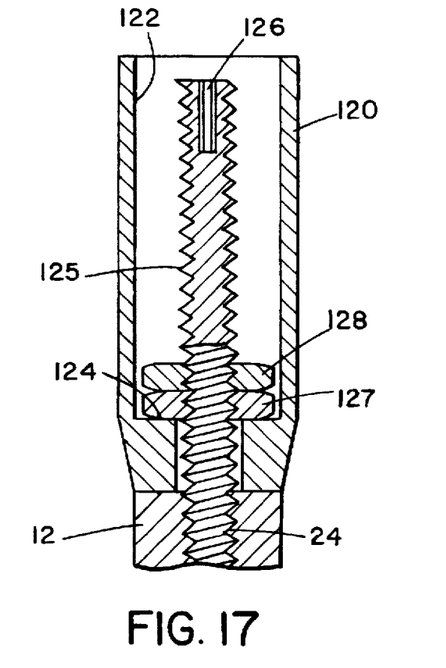
FIG. 17 is a sectional view similar to FIG. 12 illustrating another embodiment of the invention.

FIG. 17 of the drawings illustrates an implant attachment assembly and locking device according to another embodiment of the invention. In this embodiment, post or cylinder 120 has a through bore 122 of stepped diameter with shoulder or seat 124, and a headless fastener screw 125 comprising an elongate, threaded shaft projects through the bore 122 for threaded engagement in the threaded bore 24 of implant 12. A hex bore 126 is provided in the upper end of screw 125 for receiving a suitable tool for tightening the screw in bore 24. Rather than having an integral head as in the previous embodiments, the screw 125 in this version has a primary fastening nut 127 tightened on the threaded shaft. The nut 127 engages seat 124 when the screw 125 is tightened in bore 24. A second, locking nut 128 is then tightened onto the shaft and tightened down so that its lower surface is in close, frictional engagement with the upper surface of the first nut 127, resisting loosening of the assembly. The opposing faces of the two nuts may have roughened surfaces or the like, as described above in connection with FIGS. 4 and 5.

Figure 18:
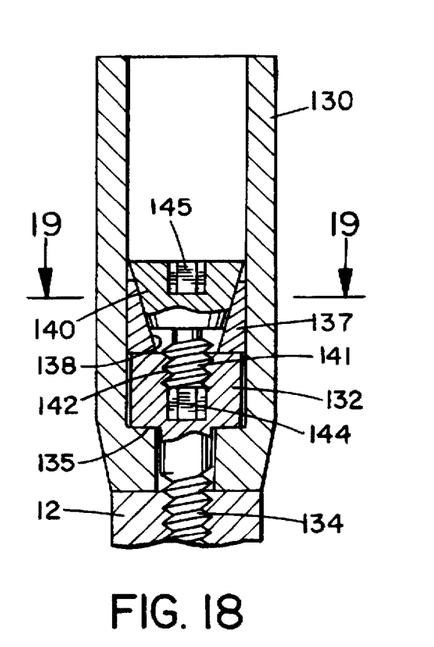
FIG. 18 is a sectional view similar to FIG. 17 illustrating another modified embodiment.
Figures 19, 21:
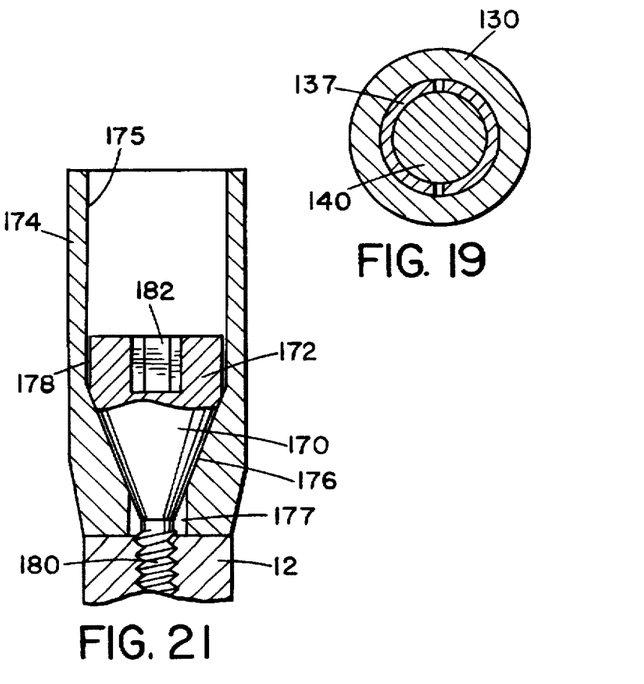
FIG. 19 is a sectional view taken on line 19—19 of FIG. 18.
FIG. 21 is a sectional view similar to FIG. 20 illustrating a modification.

FIGS. 18 and 19 illustrate another alternative attachment assembly and locking device which can be retro-fitted into an existing post without any modification to the post bore. In this embodiment, post 130 is secured to implant 12 by means of a primary fastening screw having a head 132 and threaded shaft 134 for threaded engagement in the implant bore. Post 130 has a through bore with a step or seat 135 as in the previous embodiments, against which the head 132 is seated when the primary screw is secured in the implant bore.

The locking device in this embodiment comprises a partially split washer 137 having a downwardly tapering, conical through bore 138, and a locking screw 139 having a conical head 140 for mating engagement in the washer bore 138, and a threaded shaft 141 for threaded engagement in a correspondingly threaded portion 142 of a bore in the upper face of the primary screw. The washer is split along at least part of its length, as illustrated in FIG. 19. The washer bore 138 and screw head 140 have a matching taper of between 6° and 20° The primary screw bore has a threaded upper end portion 142, and a hex portion 144 at its lower end for engagement with a suitable screw tightening tool.

In order to install this assembly, the primary screw is first inserted into the post bore and a suitable hex tool is engaged in hex portion 144 in order to tighten the shaft 134 into the implant bore and tighten head 132 against seat 135. The washer 137 and locking screw combination is then inserted into the bore above the head 132 of the primary screw. Head 140 has a hex bore 145 at its upper end for receiving the end of a suitable tool for tightening shaft 141 into the upper threaded portion 142 of the primary screw bore. As the locking screw is tightened down into the bore in the primary screw head, it will simultaneously bear against the split part of washer 137, urging the two halves apart and into close mating engagement with the surface of the post bore, while the lower end face of washer 137 is also urged downwardly into close mating engagement with the upper face of screw head 132. The frictional engagement between these surfaces will help to resist loosening of the primary fastening screw. The washer 137 may be of any suitable material such as metal or more resilient material.

Figure 20:
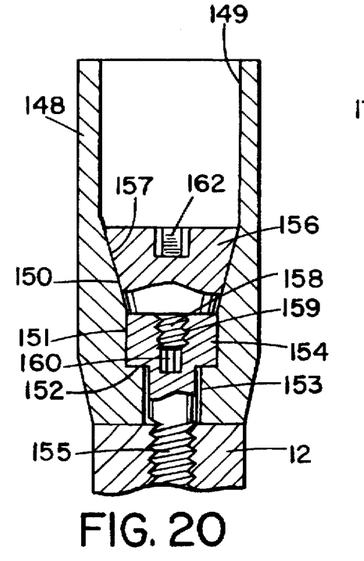
FIG. 20 is a sectional view similar to FIG. 17 illustrating another modified attachment assembly and locking device.

FIG. 20 illustrates another modified embodiment in which post 148 has a through bore 149 having a downwardly tapered, frusto-conical portion 150 leading from a larger diameter portion of the bore to a smaller diameter portion 151. A step or seat 152 is provided at the lower end of bore portion 151 leading to the smallest diameter, lower end portion 153 of the bore. The primary fastening screw has an elongated head 154 of diameter substantially matching that of the intermediate bore portion 151, and a shaft 155 having screw threads for threaded engagement in the implant bore, as in the previous embodiment, with head 154 seated against step 152. A locking insert 156 having a frusto-conical surface 157 of taper matching that of the tapered portion 150 of the post bore is jammed into the bore above the head 154 of the fastening screw. Insert 156 has a threaded shaft 158 for threaded engagement in an upper, threaded portion 159 of a bore in the upper face of the screw head. The lower end of the bore comprises a hex portion 160 for receiving a suitable hex tool. The upper end face of insert 156 also has a hex bore or recess 162.

In order to secure the post 148 to an implant 12, the primary fastening screw is inserted through the post bore and the shaft is screwed into the threaded implant bore until the head is closely seated against shoulder 152. The screw is tightened by means of a suitable hex tool engaging in the hex-shaped lower end portion 160 of the bore in the screw head. Once the screw has been securely fastened, the tool is removed and the insert 156 is placed into the bore above the fastening screw, with shaft 158 threaded into the threaded portion 159 of the screw head bore by means of a hex tool engaging in hex bore 162 to tighten the insert down until the mating tapered surfaces 150 and 157 are in close engagement. The implant member is compressed against the tapered surface 150 and forms a cold weld with that surface, locking the parts together and resisting loosening of the primary fastening screw.

FIG. 21 illustrates a modification of the previous embodiment, in which a tapered surface 170 is provided on the head 172 of the primary fastening screw, and the separate insert member is eliminated. Instead, the head of the primary fastening screw has been modified to perform the function of the insert 156 of the previous embodiment. In this embodiment, the post 174 has a bore with an upper portion 175 of a first diameter, a tapered portion 176 with a taper matching that of the tapered surface 170 of the screw, and a lower end portion 177 of reduced diameter. The screw head 172 has an upper portion 178 of diameter matching that of the upper portion 175 of the post bore, and a threaded shaft 180 projecting downwardly from the tapered surface 170 through bore portion 177 for threaded engagement in the bore of implant 12. The tolerance between the screw head 172 and the inner diameter of the bore in post 174 is very tight. Screw head 172 has a hex-shaped bore or receptacle 182 at its upper end for receiving a suitable tool for tightening the screw in the post. The upper end portion 178 of the screw head 172 may be extended up to fill the entire post bore if desired, and the length of portion 178 may be adjusted as necessary depending on the height of the post.

The fastening screw is inserted into the post so that the threaded shaft projects out of the lower bore portion 177. A suitable tool is engaged in hex bore 182 and the screw is tightened into the threaded bore of implant 12. Simultaneously, the tapered surface 170 is pushed against the matching portion 176 of the bore, pushing outward against the tapered portion 176 and creating frictional engagement between the screw head and post bore. An effective cold weld is formed between the tapered surfaces, thus resisting loosening of the fastening screw.

In each of the embodiments of FIGS. 18–21, the taper of the opposing tapered surfaces is between 6° and 20°. This allows a cold weld to be formed between the opposing surfaces, resisting loosening or backing out of the primary screw. FIGS. 20 and 21 illustrate how a separate insert member can be eliminated and the head of the primary screw can be modified to perform the same function as the separate insert member. Some of the previous embodiments can be modified in an equivalent manner to provide the locking function on the screw head instead of a separate insert member, for example the embodiments of FIGS. 9–16. However, the first two embodiments require a separate insert member.

The locking inserts of the above embodiments will all resist loosening of the primary fastening screw attaching a prosthetic dental device to an implant. Thus, the risk of such prosthetic devices becoming loose, unstable and uncomfortable is significantly reduced. Another advantage of the insert arrangement is that the insert will fill the space in the post above the fastening screw, preventing or reducing the risk of saliva ingress and potential bacterial contamination. The insert arrangement is compatible with all existing implant devices.

Although some preferred embodiments of the invention have been described above by way of example only, it will be understood by those skilled in the field that modifications may be made to the disclosed embodiments without departing from the scope of the invention, which is defined by the appended claims.

I claim:

1. An implant attachment locking assembly, comprising:
   a post member for securing to a dental prosthesis, the post member having an upper end, a lower end, and a through bore extending between the upper and lower ends, the through bore having a step in diameter forming an upwardly facing seating shoulder;
   a fastening screw having a head seated in the through bore against the seating shoulder and a threaded shaft projecting out of the through bore through the lower end of the post member for releasable engagement in an implant bore, the screw head having an upper face;
   an insert member fitting in the through bore above the fastening screw, the insert member having a lower end face facing the upper face of the screw head for abutment with the upper face of the screw head;
   the insert member having a locking mechanism for engaging the through bore to releasably secure the insert member in a locking position in the through bore in which the lower face of the insert member abuts against the upper face of the screw head to resist loosening of the screw;
   the upper face of the screw head having a recess for receiving a tool for adjusting the tightness of the screw;
   the insert member having a through bore for allowing access to the tool receiving recess in the screw head;
   the locking mechanism comprising a first fastener formation on the insert member and the most member through bore having a second fastener formation for mating engagement with the first fastener formation to secure the insert member in the locking position; and
   the fastener formations on the insert member and through bore comprising mating screw threads, and the screw threads on the insert member being of different dimensions to the screw threads on the screw shaft.

2. The assembly as claimed in claim 1, wherein the insert member substantially fills the post through bore from the fastening screw up to the upper end of the post member.

3. The assembly as claimed in claim 1, wherein the screw threads on the insert member extend along at least part of the length of the insert member from the lower end of the insert member.

4. The assembly as claimed in claim 3, wherein the screw threads extend for at least 1.5 mm.

5. The assembly as claimed in claim 3, wherein the screw threads on the screw shaft have a first depth and the screw threads on the insert member have a second depth different from the first depth.

6. The assembly as claimed in claim 1, wherein the screw threads on the insert member and through bore have a different pitch from the screw threads on the screw shaft.

7. The assembly as claimed in claim 1, wherein:
   the upper face of the screw head and the lower face of the insert member have roughened surfaces.

8. The assembly as claimed in claim 1, wherein the upper face of the screw head and the lower face of the insert member are ribbed surfaces.

9. An implant attachment locking assembly, comprising:
   a post member for securing to a dental prosthesis, the post member having an upper end, a lower end, and a through bore extending between the upper and lower ends, the through bore having a step in diameter forming an upwardly facing seating shoulder;
   a fastening screw having a head for seating in the through bore against the seating shoulder and a threaded shaft projecting out of the through bore through the lower end of the post member for releasable engagement in an implant bore, the screw head having an upper face;
   an insert member for fitting in the through bore above the fastening screw, the insert member having a lower face facing the upper face of the screw head;
   the insert member having a locking mechanism for engaging the through bore to releasably secure the insert member in a locking position in the through bore in which the lower face of the insert member abuts against the upper face of the screw head to resist loosening of the screw;
   the locking mechanism comprising a first fastener formation on the insert member, and the through bore having a second fastener formation for mating engagement with the first fastener formation to secure the insert member in the locking position;
   the first mating formations comprising a plurality of spaced, outwardly projecting bayonet lugs on the lower end of the insert member; and
   the second mating formations comprising a plurality of bayonet grooves extending along the through bore for slidably receiving the respective bayonet lugs, each bayonet groove having a lower end spaced above the upper face of the screw head and a circumferentially extending bayonet slot extending from the lower end for receiving the respective lug in a rotated, locked position of the insert member.

10. The assembly as claimed in claim 9, wherein the bayonet slots are inclined downwardly.

11. The assembly as claimed in claim 9, wherein the bayonet lugs have downwardly inclined lower faces.

12. An implant attachment locking assembly, comprising:
   a post member for securing to a dental prosthesis, the post member having an upper end, a lower end, and a through bore extending between the upper and lower ends, the through bore having a step in diameter forming an upwardly facing seating shoulder;
   a fastening screw having a head seated in the through bore against the seating shoulder and a threaded shaft projecting out of the through bore through the lower end of the post member for releasable engagement in an implant bore, the screw head having an upper face;

an insert member for fitting in the through bore above the fastening screw, the insert member having a lower face facing the upper face of the screw head for abutment with the upper face of the screw head;

the insert member having a locking mechanism for engaging the through bore to releasably secure the insert member in a locking position in the through bore in which the lower face of the insert member abuts against the upper face of the screw head to resist loosening of the screw;

the locking mechanism comprising a first fastener formation on the insert member, and the through bore having a second fastener formation for mating engagement with the first fastener formation to secure the insert member in the locking position; and the insert member having an outer surface facing the through bore, the outer surface having at least one radially outwardly facing cut-out at a location in its length, and the first mating formation comprising at least one ball bearing slidably mounted in the cut-out for movement between a retracted position in which the entire ball bearing is within the cut-out, and an extended, locking position in which the ball bearing projects partially out of the cut-out, and actuator means in the insert member for urging the ball bearing outwardly into the locking position, and the second mating formation comprising an annular groove in the through bore for receiving the ball bearing in the extended position when the insert member is in said locking position, whereby the insert member is releasably secured in said through bore.

13. The assembly as claimed in claim 12, wherein said insert member has a through bore intersecting said cut out, and an actuating member extending through said bore for engaging said ball bearing, the actuating member having a beveled end face comprising said actuator means, whereby the ball bearing is urged outwardly as the actuating member is moved downwardly in said bore.

14. The assembly as claimed in claim 12, wherein said actuator means comprises a cam member for engaging said ball bearing.

15. An implant attachment locking assembly, comprising:

a post member for securing to a dental prosthesis, the post member having an upper end, a lower end, and a through bore extending between the upper and lower ends, the through bore having a step in diameter forming an upwardly facing seating shoulder;

a fastening screw having a head seated in the through bore against the seating shoulder and a threaded shaft projecting out of the through bore through the lower end of the post member for releasable engagement in an implant bore, the screw head having an upper face;

an insert member for fitting in the through bore above the fastening screw, the insert member having a lower end face facing the upper face of the screw head for abutment with the upper face of the screw head;

the insert member having a locking mechanism for engaging the through bore to releasably secure the insert member in a locking position in the through bore in which the lower face of the insert member abuts against the upper face of the screw head to resist loosening of the screw;

the upper face of the screw head having a recess for receiving a tool for adjusting the tightness of the screw;

the insert member having a through bore for allowing access to the tool receiving recess in the screw head;

said insert member having an expandable outer sleeve and internal actuating means for biassing said sleeve outwardly into an expanded position in which said sleeve is in close frictional engagement with said through bore, said expanded sleeve comprising said locking mechanism.

16. The assembly as claimed in claim 15, wherein said insert member comprises two semi-cylindrical parts having opposing flat faces, said sleeve comprising a resilient, C-shaped member enclosing said two parts to retain them together, the flat faces of said parts having aligned recesses forming an actuator bore, and an actuator member in said bore, said actuator member being rotatable between an inoperative position and an operative position in which said opposing parts are urged away from one another to bias said sleeve outwardly into said expanded position.

17. The assembly as claimed in claim 16, wherein said actuator member comprises a cam for bearing against the surface of at least one of said recesses to urge said parts away from one another and expand said sleeve, into said operative, locked position.

18. The assembly as claimed in claim 15 including a separate intermediate joiner disc for locating between said insert member and screw head, the screw head having a recess in its upper face, and the joiner disc having a projecting boss shaped and dimensioned for mating engagement in said recess.

19. An implant attachment locking assembly, comprising:

a post member for securing to a dental prosthesis, the post member having an upper end, a lower end, and a through bore extending between the upper and lower ends, the through bore having a step in diameter forming an upwardly facing seating shoulder;

a fastening screw having a head for seating in the through bore against the seating shoulder and a threaded shaft projecting out of the through bore through the lower end of the post member for releasable engagement in an implant bore, the screw head having an upper face;

an insert member for fitting in the through bore above the fastening screw, the insert member having a lower face facing the upper face of the screw head for abutment with the upper face of the screw head;

the insert member having a locking mechanism for engaging the through bore to releasably secure the insert member in a locking position in the through bore in which the lower face of the insert member abuts against the upper face of the screw head to resist loosening of the screw;

the upper face of the screw head having a recess for receiving a tool for adjusting tightness of the screw;

the insert member having a through bore for allowing access to the tool receiving recess in the screw head; and the insert member having an annular skirt depending downwardly from the lower face for wedged engagement between the screw head and post member bore.

20. The assembly as claimed in claim 19, wherein the skirt has a plurality of slots around its periphery.

21. The assembly as claimed in claim 20, wherein the skirt is tapered inwardly.

22. An implant attachment locking assembly, comprising:

a post member for securing to a dental prosthesis the post member having an upper end, a lower end, and a through bore extending between the upper and lower ends, the through bore having a step in diameter forming an upwardly facing seating shoulder;

a fastening screw having a head seated in the through bore against the seating shoulder and a threaded shaft projecting out of the through bore through the lower end of the post member for releasable engagement in an implant bore, the screw head having an upper face;

an insert member fitting in the through bore above the fastening screw, the insert member having a lower end face facing the upper face of the screw head for abutment with the upper face of the screw head;

the insert member having a locking mechanism for engaging the through bore to releasably secure the insert member in a locking position in the through bore in which the lower face of the insert member abuts against the upper face of the screw head to resist loosening of the screw;

the upper face of the screw head having a recess for receiving a tool for adjusting the tightness of the screw;

the insert member having a through bore for allowing access to the tool receiving recess in the screw head;

the locking mechanism comprising a first fastener formation on the insert member, and the through bore in the post member having a second fastener formation for mating engagement with the first fastener formation to secure the insert member in the locking position; and the interchanging fastener formations on the insert member and post member bore being coated with a resilient material.

23. A method of securing a prosthetic device to an implant via a primary screw and resisting loosening of the primary screw, comprising the steps of:

inserting a primary fastening screw having a head and a threaded shaft through a bore in a post secured to a prosthetic device so that the threaded shaft of the screw projects out through the end of the post;

using a tool engaging the head of the screw to tighten the threaded shaft in a correspondingly threaded bore of an implant or implant abutment;

inserting a locking device into the through bore in the post above the screw into a first position prior to a locking position in which the lower end face of the locking device is in close frictional engagement with an upper end face of the primary fastening screw to resist rotation of the screw;

inserting the tool through a through bore in the locking device to engage the head of the screw and tighten the screw further into the implant or implant abutment until it reaches a fully engaged position in the implant bore; and securing the locking device in the locking position, whereby the locking device resists loosening of the screw.

24. The method as claimed in claim 23, including the step of cutting the locking device to a predetermined length corresponding to the length of the post bore above the head of the fastening screw.

25. The method as claimed in claim 23, including the steps of cutting threads in a portion of a prosthetic post through bore which match threads on the outer surface of the locking device, and threading the locking device into the threaded through bore portion into locking engagement with the screw head.

26. An implant attachment locking assembly, comprising:

a post member for securing to a dental prosthetic device, the post member having an upper end, a lower end, and a through bore extending between the upper and lower ends, the through bore having a step in diameter forming an upwardly facing seating shoulder;

a fastening screw having a threaded shaft for projecting out of the through bore through the lower end of the post member for releasable engagement in an implant bore and a retainer device positioned in the through bore and engaging the seating shoulder to secure the prosthetic device to the threaded shaft and implant;

an insert member fitting in the through bore above the retainer member;

the insert member having a locking mechanism for releasably securing the insert member in a locking position in the through bore in which the insert member abuts against the retainer device to resist loosening of the screw; and the fastening screw comprising a headless screw shaft and the retainer device comprising a first nut threadably engaged on the screw shaft for seating engagement on the seating shoulder when the shaft is threadably secured in the implant bore.

27. The assembly as claimed in claim 26, wherein the insert member comprises a second, lock nut for threaded engagement on the screw shaft above the first nut, the lock nut having a lower face for frictional engagement with the first nut to resist loosening of the screw.

28. An implant attachment locking assembly, comprising:

a post member for securing to a dental prosthetic device, the post member having an upper end, a lower end, and a through bore extending between the upper and lower ends, the through bore having a step in diameter forming an upwardly facing seating shoulder;

a fastening screw having a threaded shaft for projecting out of the through bore through the lower end of the post member for releasable engagement in an implant bore and a head for engaging the seating shoulder and securing the prosthetic device to the implant, the head having an upper face with a threaded bore extending downwardly from the upper face; and an insert member for fitting into the through bore above the fastening screw, the insert member having a screw shaft for threaded engagement in the threaded bore in the screw head, and a locking mechanism for releasably securing the insert member against opposing portions of the post member through bore to resist loosening of the screw.

29. The assembly as claimed in claim 28, wherein the post member through bore has a tapered surface extending over a portion of its length spaced from the upper end and from the seaming shoulder, and the insert member has a tapered locking portion with a taper matching that of the tapered surface of the through bore for close frictional engagement with the tapered surface when the insert member is fully engaged with the threaded bore in the screw head, the tapered locking portion and tapered surface comprising said locking mechanism.

30. The assembly as claimed in claim 28, wherein the locking mechanism comprises a split washer for fitting into the through bore above the fastening screw, the split washer having a through bore with a tapered inner surface, the insert member having a head with a tapered outer surface for mating engagement with the tapered inner surface of the split washer, whereby the split washer is urged outwardly into engagement with the post member through bore to resist loosening of the screw.

* * * * *

UNITED STATES PATENT AND TRADEMARK OFFICE
CERTIFICATE OF CORRECTION

PATENT NO. : 5,733,122
DATED     : March 31, 1998
INVENTOR(S) : GORDON, Basil

It is certified that error appears in the above-indentified patent and that said Letters Patent is hereby corrected as shown below:

- Column 11, claim 1, line 56: after "the" (second occurrence) delete "most" and insert --post-- instead;
- Column 15, claim 22, line 27: after "the" (first occurrence) delete "interchanging" and insert --interengaging-- instead; and
- Column 16, claim 29, line 50: after "the" (first occurrence) delete "seaming" and insert --seating-- instead.

Signed and Sealed this

Fourteenth Day of July, 1998

*Attest:*

BRUCE LEHMAN

*Attesting Officer*      *Commissioner of Patents and Trademarks*